(12) United States Patent
Godbole et al.

(10) Patent No.: US 6,204,407 B1
(45) Date of Patent: Mar. 20, 2001

(54) AMMOXIDATION OF A MIXTURE OF ALCOHOLS TO A MIXTURE OF NITRILES TO ACETONITRILE AND HCN

(75) Inventors: Sanjay P. Godbole, Solon, OH (US); Michael J. Seely, Naperville, IL (US); Dev D. Suresh, Hudson, OH (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/517,404

(22) Filed: Mar. 2, 2000

Related U.S. Application Data

(63) Continuation-in-part of application No. 09/208,053, filed on Dec. 9, 1998, now abandoned.

(51) Int. Cl.[7] ................................................. C07C 253/00
(52) U.S. Cl. ........................................... 558/319; 558/323
(58) Field of Search ..................................... 558/319, 323

(56) References Cited

U.S. PATENT DOCUMENTS 3,911,089 * 10/1975 Shiraishi et al. ..................... 423/376
4,485,079 * 11/1984 Brazdil et al. ....................... 423/376

* cited by examiner

*Primary Examiner*—Joseph K. McKane
*Assistant Examiner*—Joseph Murray
(74) *Attorney, Agent, or Firm*—Thomas E. Nemo

(57) ABSTRACT

A process for increasing the yield of one or both co-products HCN and acetonitrile produced during the manufacture of acrylonitrile comprising introducing a hydrocarbon selected from the group consisting of propylene and propane, a mixture comprising one or more alcohols selected from crude methanol, crude ethanol or crude propanol, ammonia and air into a reaction zone containing an ammoxidation catalyst, reacting the hydrocarbon, alcohol, ammonia and oxygen over said catalyst at an elevated temperature to produce acrylonitrile, hydrogen cyanide and acetonitrile, and recovering the acrylonitrile, hydrogen cyanide and acetonitrile from the reactor.

21 Claims, No Drawings

AMMOXIDATION OF A MIXTURE OF ALCOHOLS TO A MIXTURE OF NITRILES TO ACETONITRILE AND HCN

CROSS-REFERENCE TO RELATED APPLICATIONS

This application is a continuation-in-part of U.S. patent application Ser. No. 09/208,053 filed Dec. 9, 1998 now abandoned.

BACKGROUND OF THE INVENTION

The present invention is directed to a novel process for the ammoxidation of a mixture of alcohols to a mixture of nitriles. In particular, the present invention is directed to increasing the yield and, preferably, the ratio of co-product hydrogen cyanide and acetonitrile produced during the ammoxidation of propylene to acrylonitrile.

There are several patents which address the issue of the injection of methanol or ethanol into a fluid bed reactor to produce hydrogen cyanide or acetonitrile. In addition, these references further disclose that the methanol or ethyl alcohol may be introduced into a fluid bed reactor to increase the co-product hydrogen cyanide or acetonitrile while manufacturing acrylonitrile. For example, U.S. Pat. Nos. 3,911,089; 4,485,079 and 5,288,473 are directed to the ammoxidation of methanol to produce hydrogen cyanide by injection of the methanol into the fluid bed reactor containing the ammoxidation catalyst suitable for the manufacture of acrylonitrile. Each of these references teach that methanol injection can be made simultaneously with the manufacture of acrylonitrile. In addition, Japanese Patent Applications 74-87,474; 79-08,655; and 78-35,232 relate to similar methods of increasing the yield of hydrogen cyanide during the manufacture of acrylonitrile. Japanese Patent Application 2[1990]-38,333 is directed to improving acetonitrile yields by injecting acetone and/or ethyl alcohol into an ammoxidation reactor containing ab ammoxidation catalyst. The process disclosed in the Japanese Patent Application includes simultaneously injecting the acetone and/or ethyl alcohol into the ammoxidation reactor while manufacturing acrylonitrile. All of these patents are concerned with the production of either additional hydrogen cyanide or acetonitrile.

The present invention is directed to a process which increases the yield of one or both main co-products (i.e. HCN and acetonitrile) during the manufacture of acrylonitrile while (1) saving on the raw material costs associated with the increase in co-product yields and (2) achieving the same or better conversion and selectivity to the desired co-products (on a carbon basis) as one obtains with the use of neat alcohols such as methanol/ethanol. The relative amounts of hydrogen cyanide and acetonitrile can be controlled by the process of this invention.

We have found, unexpectedly, that the use of crude alcohol mixtures can attain a desirable increase in the production of acetonitrile and hydrogen cyanide during the production of acrylonitrile.

SUMMARY OF THE INVENTION

It is the primary object of the present invention to provide a process for substantially increasing the yields of one or more of the co-products hydrogen cyanide and acetonitrile produced during the manufacture of acrylonitrile from propylene or propane.

It is an object of the present invention to provide a process for the conversion of a mixture of crude alcohol containing methanol, ethanol, other alcohols and water into hydrogen cyanide and acetonitrile during the manufacture of acrylonitrile without substantially affecting the yield of the acrylonitrile.

It is a further object of this invention to provide a process for the conversion of an alcohol comprising ethanol into acetonitrile, with or without the inclusion of methanol. Methanol can be included in the ethanol in an amount desired to adjust the relative amounts of hydrogen cyanide and acetonitrile co-products that are produced. Thus, when the need for hydrogen cyanide increases, methanol or additional methanol can be added to the ethanol feed mixture to achieve enhanced amounts of hydrogen cyanide. Alternatively, if additional production of acetonitrile is desired relative to hydrogen cyanide, the amount of ethanol in the alcohol feed can be increased to enhance the relative amount of acetonitrile produced.

Additional objects and advantages and novel features of the invention will be set forth in part in the description which follows, and in part will become apparent to those skilled in the art upon examination of the following, or may be learned by the practice of the invention. The objects and advantages of the invention may be realized and attained by means of the instrumentalities and combinations particularly pointed out in the appended claims.

To achieve the foregoing objects in accordance with the purpose of the present invention as broadly described herein, the method of the present invention comprises introducing a hydrocarbon selected from the group consisting of propylene and propane, a crude alcohol comprising a mixture of $C_1$ to $C_4$ alcohols, ammonia and oxygen-containing gas into reaction zone (e.g. fluid bed reactor) to react in the presence of a catalyst (e.g. fluid bed catalyst) to produce a reactor effluent comprising acrylonitrile, hydrogen cyanide and acetonitrile, passing the reactor effluent containing acrylonitrile, hydrogen cyanide and acetonitrile into a quench column to cool the reactor effluent, and recovering the acrylonitrile, acetonitrile and hydrogen cyanide from the quench column.

In a preferred embodiment of the present invention, the mixture of crude alcohols is supplied using crude ethanol, crude propanol and/or crude methanol. For purposes of the present invention, crude ethanol includes a mixture of alcohols comprising ethanol, propanol, butanol and water. A typical source of commercially available crude ethanol contains 86.34% ethanol, 1.025% I-propanol, 1.266% N-butanol and 11.37% water. While not being particularly limited to this composition, any crude ethanol, propanol and/or methanol mixture is suitable in the practice of the present invention. It is preferred that the crude alcohol also contains water, preferably at least about 3 weight percent, more preferably at least about 5 weight percent, thereby further reducing the cost of operation of the process of the present invention. One of the unexpected benefits of the practice of the present invention is the discovery that the co-product selectivity and conversion results obtained utilizing a crude alcohol are the same or better (on a carbon to carbon basis) when compared to the results obtained using a pure alcohol feed.

In the practice of the present invention, it is envisioned that any ammoxidation catalyst can be utilized to achieve the desired results of increasing the yield of co-product acetonitrile and hydrogen cyanide. Typical ammoxidation catalysts can be generalized by the following two formulae:

$$A_aB_bC_cD_dMo_{12}O_x$$

where
- A=Li, Na, K, Cs, Tl and combinations thereof, preferably Cs and K
- B=Ni, Co, Mn, Mg, Ca and combinations thereof, preferably Ni, Co and Mg
- C=Fe, Cr, Ce, Cu, V, Sb, W, Sn, Ga, Ge, In, P and combinations thereof, preferably Fe, Cr and Ce
- D=Bi and/or Te, preferably Bi
- a=0.14.0, preferably 0.1 to 0.5, especially preferred being 0.1 to 0.2
- b=0.1–10.0, preferably 5 to 9, especially preferred being 6 to 8, and
- c,d=0.1–10.0, preferably 0.5 to 4, especially preferred being 0.5 to 3;

and

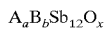

where
- A=Fe, Cr, Ce, V, U, Sn, Ti, Nb and combinations thereof, preferably Fe, V, Sn and Ti
- B=Mo, W, Co, Cu, Te, Bi, Zn, B, Ni, Ca, Ta and combinations thereof, preferably Mo and Cu
- a=0.1–16, preferably 2 to 12, especially preferred being 4 to 10
- b=0.0–12, preferably 1 to 10, especially preferred being 2 to 6, and the value of x depends on the oxidation state of the elements used.

The catalyst can be used either unsupported, or be supported with silica, alumina, titania, zirconia and the like; however, silica is the preferred support. Typically, catalysts envisioned as suitable in the practice of the present invention are disclosed in U.S. Pat. Nos. 3,642,930; 4,485,079; 3,911,089; 4,873,215; 5,134,105 and 5,093,299, herein incorporated by reference.

Reference will now be made in detail to the present preferred embodiments of the invention.

DETAILED DESCRIPTION OF THE INVENTION

The present invention is directed to the utilization of crude alcohols containing a mixture of $C_1$ through $C_4$ alcohols as a source for the production of useful nitrile co-products (hydrogen cyanide and acetonitrile) produced during the manufacture of acrylonitrile. In addition, crude alcohols containing substantial amounts of diluents such as water may be utilized in the practice of the present invention thereby further reducing the cost of the raw materials suitable for the production of viable co-products.

In one aspect, the present invention involves a process for increasing the yield of one or both HCN and acetonitrile during the manufacture of acrylonitrile comprising introducing a hydrocarbon selected from the group consisting of propylene and propane, a crude alcohol comprising a mixture of methanol, ethanol or propanol, ammonia and air, into a reaction zone containing an ammoxidation catalyst, reacting the hydrocarbon, alcohol, ammonia and oxygen over said catalyst at an elevated temperature to produce acrylonitrile, hydrogen cyanide and acetonitrile, and recovering the acrylonitrile, hydrogen cyanide and acetonitrile from the reactor.

As used herein, crude ethanol preferably means a mixture, optionally containing water, comprising about 5 to about 95 weight percent ethanol, preferably about 5 to about 94 weight percent ethanol, more preferably about 50 to about 90 weight percent ethanol. The other components can be, for example, water, methanol, C3–C4 alcohols as well as other organic compounds. Preferably, however, the other components are selected from one or more of water and alcohols, particularly those alcohols identified above. As used herein, crude propanol means a mixture, optionally containing water, comprising about 5 to about 99 weight percent of one or more propanols, preferably about 50 to about 95 weight percent of one or more propanols. Typically, the propanol, particularly the crude propanol, is a mixture of propanols mixture which is at least about 50 weight percent, more preferably at least about 75 weight percent isopropanol. As used herein, crude methanol preferably means a mixture comprising up to about 98 weight percent methanol, preferably up to about 97 weight percent methanol and more preferably up to about 95 weight percent methanol. Water, if present in the alcohols, can be about 0.1 to about 10 weight percent, preferably 3 to about 10 weight percent based on the amount of alcohol and water present.

As mentioned above, in one embodiment of this invention, the relative amounts of hydrogen cyanide and acetonitrile produced by the process of this invention can be adjusted by adjusting the relative amounts of methanol compared to ethanol added to the reaction zone in the acrylonitrile process. Thus if greater amounts of hydrogen cyanide are desired, the ratio of methanol to ethanol can be increased. Conversely, if less hydrogen cyanide is desired, the ratio can be reduced. This invention is, therefore, a process for adjusting the relative amounts of hydrogen cyanide and acetonitrile produced during the manufacture of acrylonitrile by adding a mixture comprising methanol, ethanol or propanol and by controlling the ratio of methanol and ethanol or propanol, preferably ethanol, added to the acrylonitrile reaction zone. While any grade of methanol, ethanol or propanol can be used in this embodiment, even highly pure methanol, ethanol or propanol, it is advantageous to use crude methanol, ethanol, or propanol, preferably crude methanol, ethanol and crude propanol as described hereinabove. This invention, therefore, is also a process for adjusting the relative amounts of hydrogen cyanide and acetonitrile produced during the manufacture of acrylonitrile comprising introducing a hydrocarbon selected from the group consisting of propane and propylene, ammonia, air and an alcohol mixture comprising methanol and a second alcohol comprising ethanol, propanol or mixtures thereof, in a reaction zone containing an ammoxidation catalyst, such as the catalysts described herein, reacting the hydrocarbons, alcohols, ammonia, and oxygen over said catalyst at an elevated temperature to produce acrylonitrile, hydrogen cyanide, and acetonitrile, and recovering acrylonitrile, hydrogen cyanide, and acetonitrile from the reaction, where the weight ratio of methanol to second alcohol in the alcohol mixture is suitably about 99:1 to about 1:99, preferably about 98:2 to about 2:98, more preferably about 95:5 to about 5:95. In the alcohol mixture, preferably the weight ratio of methanol to ethanol, or methanol to propanol, or methanol to a combination of ethanol and propanol, is suitably about 99:1 to about 1:99, preferably about 98:2 to about 2:98, more preferably about 95:5 to about 5:95. As an example, if it is desired to co-manufacture a relatively larger amount of hydrogen cyanide compared to the amount of acetonitrile, the alcohol ratio fed to the reactor may, for example, be 90 weight percent ethanol and 10 weight percent methanol. Or, if it is desirable to increase the amount of hydrogen cyanide, the alcohol ratio fed to the reactor may be 10 weight percent ethanol and 90 weight percent methanol. It is understood that the mixture of alcohols fed to the acrylonitrile reactor can be mixed prior to entering the reactor or the different alcohols can be added separately and mixed in the reactor itself. In the most preferred embodiment of this invention, crude ethanol is used as the source of ethanol and methanol is added to the crude ethanol to achieve a desired ratio of hydrogen cyanide and acetonitrile co-products.

In the preferred embodiment of the present invention, it is necessary that the reactor conditions be adjusted to obtain the increased yield in acetonitrile and hydrogen cyanide obtained by utilizing the mixture of crude alcohol. In the practice of the present invention, the ammoxidation reaction conditions preferably should be within the following parameters: Crude alcohol is between 1 and 50% of propylene or propane rate on a total carbon basis. The temperature of the reaction is between 410° to 460° C., preferably 430° to 460° C. Typically, the pressure is maintained at between 1 to 5 atmospheres with 1 to 3 atmospheres being preferred.

In a further preferred embodiment of the present invention, the crude alcohol mixture comprises a mixture containing ethanol, isopropanol, butanol and water.

In a still further embodiment of the present invention, the process is performed in a fluid bed reactor.

U.S. patent application Ser. No. 09/208,053 filed Dec. 9, 1998, is hereby specifically incorporated by reference in its entirety.

The following examples are set forth below for illustrative purposes and are not considered as limiting to the practice of the present invention. The catalyst utilized in all of the examples was a promoted $BiFeMoO_x$ known for its suitability in the ammoxidation of propylene to acrylonitrile. Five, 10 and 15% of the propylene feed (in terms of total carbon) were replaced with crude ethanol to give the results set forth below in Table I. In each of the following examples, the reactor temperature was 440° C., the pressure was 9.5 psig and the feed ratio of propylene+alcohol/ammonia/air was 1/1.2/9.3. The wwh was 0.07 (grams of hydrocarbon/grams of catalyst, hour).

TABLE I

| Example No. | % EtOH as C Fed | % AN Yield | % Aceto Yield | % HCN Yield |
|---|---|---|---|---|
| 1(comp.) | 0 | 78.8 | 1.5 | 6.5 |
| 2 | 5 | 75.3 | 3.9 | 6.9 |
| 3 | 10 | 71.5 | 5.0 | 7.4 |
| 4 | 15 | 67.5 | 6.5 | 8.0 |

As a further example of the value of using alcohol mixtures, 30% by weight methanol was blended with the crude ethanol above and this was co-fed to the same propylene ammoxidation reactor. The results are shown below in Table II and indicate a shift towards HCN in the products. This feed should be used by a commercial plant when high production of HCN is needed.

TABLE II

| Example No. | % Blend as C Fed | % AN Yield | % Aceto Yield | % HCN Yield |
|---|---|---|---|---|
| 5(comp.) | 0 | 78.8 | 1.5 | 6.5 |
| 6 | 5 | 75.3 | 2.9 | 7.8 |
| 7 | 10 | 71.5 | 4.6 | 9.0 |
| 8 | 15 | 67.2 | 6.2 | 10.0 |

In general, all alcohols can be ammoxidized to a mixture of nitrites. The preferred alcohols include $C_1$ to $C_4$ alcohols. Alcohols containing multiple OH groups can also be used such as, for example, ethylene or propylene glycols.

While the examples are illustrative of the practice of the present invention, they are not intended to limit applicants' invention to that illustrated, and obviously, many modifications and variations may be utilized in light of the above teaching. It is intended that the scope of applicants' invention be defined by the claims appended hereto.

What we claim as our invention is:

1. A process for adjusting the relative amounts of hydrogen cyanide and acetonitrile produced during the manufacture of acrylonitrile comprising introducing a hydrocarbon selected from the group consisting of propane and propylene, ammonia, air and an alcohol mixture comprising methanol and a second alcohol comprising ethanol, propanol or mixtures thereof, in a reaction zone containing an ammoxidation catalyst, reacting the hydrocarbons, alcohols, ammonia, and oxygen over said catalyst at an elevated temperature to produce acrylonitrile, hydrogen cyanide, and acetonitrile, and recovering acrylonitrile, hydrogen cyanide, and acetonitrile from the reaction, where the weight ratio of methanol to second alcohol in the alcohol mixture is adjusted depending on the relative amounts of hydrogen cyanide and acetonitrile desired to be produced.

2. The process of claim 1 wherein the second alcohol comprises ethanol.

3. The process of claim 2 wherein the weight ratio of methanol to ethanol is about 99:1 to about 1:99.

4. The process of claim 3 wherein the weight ratio of methanol to ethanol is about 98:2 to about 2:98.

5. A process for increasing the yield of co-products HCN and acetonitrile produced during the manufacture of acrylonitrile comprising introducing a hydrocarbon selected from the group consisting of propylene and propane, an alcohol mixture comprising methanol and ethanol in a weight ratio of about 99:1 to about 1:99, ammonia and air into a reaction zone containing an ammoxidation catalyst, reacting the hydrocarbon, alcohol mixture, ammonia and oxygen over said catalyst at an elevated temperature to produce acrylonitrile, hydrogen cyanide and acetonitrile, and recovering the acrylonitrile, hydrogen cyanide and acetonitrile from the reactor.

6. The process of claim 5 wherein the weight ratio of methanol to ethanol is about 98:2 to about 2:98.

7. A process for increasing the yield of one or both co-products HCN and acetonitrile produced during the manufacture of acrylonitrile comprising introducing a hydrocarbon selected from the group consisting of propylene and propane, a mixture comprising one or more alcohols selected from crude methanol, crude ethanol or crude propanol, ammonia and air into a reaction zone containing an ammoxidation catalyst, reacting the hydrocarbon, alcohol, ammonia and oxygen over said catalyst at an elevated temperature to produce acrylonitrile, hydrogen cyanide and acetonitrile, and recovering the acrylonitrile, hydrogen cyanide and acetonitrile from the reactor.

8. The process of claim 7 wherein the feed ratio of hydrocarbon: alcohol ranges from 1:0.01 to 1:0.5, on a total carbon basis.

9. The process of claim 8 wherein the temperature ranges from 410° to 460° C.

10. The process of claim 9 wherein the temperature ranges from 430° to 450° C.

11. The process of claim 8 wherein the pressure ranges from 1 to 5 atmospheres.

12. The process of claim 10 wherein the pressure ranges from I to 5 atmospheres.

13. The process of claim 7 wherein the crude alcohol comprises crude ethanol.

14. The process of claim 7 wherein the ammoxidation catalyst comprises the following formula:

$$A_aB_bC_cD_dMo_{12}O_x$$

where
- A=Li, Na, K, Cs, Tl and combinations thereof
- B=Ni, Co, Mn, Mg, Ca and combinations thereof
- C=Fe, Cr, Ce, Cu, V, Sb, W, Sn, Ga, Ge, In, P and combinations thereof
- D=Bi and/or Te, preferably Bi
- a=0.1–4.0
- b=0.1–10.0, and
- c,d=0.1–10.0.

15. The process of claim 7 wherein the ammoxidation catalyst comprises:

$$A_aB_bSb_{12}O_x$$

where
- A=Fe, Cr, Ce, V, U, Sn, Ti, Nb and combinations thereof
- B=Mo, W, Co, Cu, Te, Bi, Zn, B, Ni, Ca, Ta and combinations thereof
- a=0.1–16,
- b=0.0–12, and
- the value of x depends on the oxidation state of the elements used.

16. The process of claim 13 wherein the crude ethanol is about 5 to about 94 weight percent ethanol.

17. The process of claim 7 wherein the crude alcohol is crude methanol.

18. The process of claim 17 wherein the crude methanol is up to about 98 weight percent methanol.

19. The process of claim 7 wherein the crude alcohol is crude propanol.

20. The process of claim 19 wherein the crude propanol is about 50 to about 95 weight percent propanol.

21. A process for increasing the yield of one or both co-products HCN and acetonitrile produced during the manufacture of acrylonitrile comprising introducing a hydrocarbon selected from the group consisting of propylene and propane, a crude alcohol comprising a crude alcohol mixture comprising at least one $C_1$ to $C_4$ alcohols, ammonia and air into a reaction zone containing an ammoxidation catalyst, reacting the hydrocarbon, alcohol, ammonia and oxygen over said catalyst at an elevated temperature to produce acrylonitrile, hydrogen cyanide and acetonitrile, and recovering the acrylonitrile, hydrogen cyanide and acetonitrile from the reactor.

* * * * *

UNITED STATES PATENT AND TRADEMARK OFFICE
CERTIFICATE OF CORRECTION

PATENT NO. : 6,204,407 B1
DATED : March 20, 2001
INVENTOR(S) : Sanjay P. Godbole, Michael J. Seely, Dev D. Suresh It is certified that error appears in the above-identified patent and that said Letters Patent is hereby corrected as shown below:

Column 3,
Line 10, "a = 0.14.0, preferably" should read -- a = 0.1-4.0, preferably --

Column 5,
Line 65, "nitrites. The preferred alcohols" should read -- nitriles. The preferred alcohols --

Column 6,
Line 61, "from I to 5 atmospheres." should read -- from 1 to 5 atmospheres. --

Signed and Sealed this

Thirtieth Day of October, 2001

Attest:

NICHOLAS P. GODICI
*Attesting Officer*   *Acting Director of the United States Patent and Trademark Office*